(12) United States Patent
Chandler et al.

(10) Patent No.: US 12,352,681 B2
(45) Date of Patent: Jul. 8, 2025

(54) APPARATUS AND METHODS FOR SAMPLE ACQUISITION

(71) Applicant: CHANDLERTEC INC., Austin, TX (US)

(72) Inventors: Van Chandler, Austin, TX (US); Joaquin Campos, Austin, TX (US)

(73) Assignee: CHANDLERTEC INC., Austin, TX (US)

( * ) Notice: Subject to any disclaimer, the term of this patent is extended or adjusted under 35 U.S.C. 154(b) by 57 days.

(21) Appl. No.: 18/514,204

(22) Filed: Nov. 20, 2023

(65) Prior Publication Data

US 2024/0248022 A1 Jul. 25, 2024

Related U.S. Application Data

(60) Continuation of application No. 17/386,742, filed on Jul. 28, 2021, now abandoned, which is a division of application No. 16/235,076, filed on Dec. 28, 2018, now Pat. No. 11,099,117.

(60) Provisional application No. 62/611,220, filed on Dec. 28, 2017.

(51) Int. Cl.
| | |
|---|---|
| *G01N 15/14* | (2024.01) |
| *C12Q 1/68* | (2018.01) |
| *G01N 15/1404* | (2024.01) |
| *G01N 15/1409* | (2024.01) |
| *G01N 15/149* | (2024.01) |

(52) U.S. Cl.
CPC .......... *G01N 15/1425* (2013.01); *C12Q 1/68* (2013.01); *G01N 15/1404* (2013.01); *G01N 15/1409* (2024.01); *G01N 2015/1415* (2013.01); *G01N 15/149* (2024.01)

(58) Field of Classification Search
None
See application file for complete search history.

(56) References Cited

U.S. PATENT DOCUMENTS

| | | | |
|---|---|---|---|
| 5,560,811 | A | 10/1996 | Briggs et al. |
| 6,042,709 | A | 3/2000 | Parce et al. |
| 6,149,787 | A | 11/2000 | Chow et al. |
| 7,024,281 | B1 | 4/2006 | Unno |
| 2004/0071602 | A1 | 4/2004 | Yiu |
| 2005/0238545 | A1 | 10/2005 | Parce et al. |
| 2006/0198765 | A1 | 9/2006 | Gjerde et al. |
| 2017/0199210 | A1 | 7/2017 | Ang et al. |

OTHER PUBLICATIONS

Office Action issued in U.S. Appl. No. 17/386,742, mailed May 25, 2023.

*Primary Examiner* — Xiaoyun R Xu
(74) *Attorney, Agent, or Firm* — Parker Highlander PLLC

(57) ABSTRACT

Apparatus and methods for sample acquisition, including for example, samples for flow cytometry systems. Certain embodiments include a plurality of plates, valves, and conduits. In particular embodiments, the plates are stacked and the conduits extend through stack of plates, and in specific embodiments each valve is in fluid communication with a conduit.

5 Claims, 11 Drawing Sheets

APPARATUS AND METHODS FOR SAMPLE ACQUISITION

CROSS-REFERENCE TO RELATED APPLICATIONS

The present application is a continuation of U.S. patent application Ser. No. 17/386,742, filed Jul. 28, 2021, which is a divisional of U.S. patent application Ser. No. 16/235,076, filed Dec. 28, 2018, now U.S. Pat. No. 11,099,117, which claims the priority benefit of U.S. provisional application No. 62/611,220, filed Dec. 28, 2017, the entire contents of which is incorporated herein by reference.

FIELD OF THE INVENTION

Embodiments of the present invention relate to apparatus, methods and systems for acquiring samples, including for example, samples for polymerase chain reaction flow cytometry systems.

BACKGROUND

The following descriptions and examples are not admitted to be prior art by virtue of their inclusion within this section Certain analysis systems, including for example polymerase chain reaction flow cytometry systems, can be operated to analyze individual samples from a plurality of containers such as wells in a multiwell plate. In order to analyze samples from a large number of sample containers, each sample is typically removed from the sample container and transported to the analysis system to be analyzed. In typical existing systems, this often requires a needle that moves from each individual sample container to aspirate the sample from one container. After aspirating a sample from one container, the needle then must be moved to a second container to aspirate an additional sample.

The amount of time that is required to aspirate a large number of samples can be significant when an aspiration needle must be moved between each container to obtain the samples. This can result in increased analysis times and affect the efficiency of such systems. Sample acquisition times can also be negatively affected by the need to clean or purge the system between samples. In addition, typical sample acquisition systems can utilize complex mechanisms to move the aspiration needle to the different sample containers. Such mechanisms can involve numerous moving components that may be susceptible to mechanical failure. This can reduce the reliability of such sample acquisition systems and result in unwanted delays in sample analysis.

While not limiting the scope of the present disclosure, various embodiments of the present invention address issues of existing systems, including efficiency and reliability factors as noted above.

SUMMARY OF THE INVENTION

Exemplary embodiments of the present disclosure relate to methods, devices and systems for acquiring samples, including for example, samples for polymerase chain reaction flow cytometry systems.

Exemplary embodiments include an apparatus for sample acquisition. In certain embodiments, the apparatus comprises: a stack of plates; a plurality of seals coupled to a first plate of the stack of plates, wherein each seal of the plurality of seals is configured to seal to a well in a well plate; a first plurality of conduits extending through the stack of plates and the plurality of seals; a plurality of gas valves, wherein each valve is in fluid communication with a conduit in the first plurality of conduits; a sample port in a second plate of the stack of plates; and a second plurality of conduits extending through the plurality of seals and the stack of plates, wherein the second plurality of conduits is in fluid communication with the sample port.

In particular embodiments, the stack of plates comprises a first valve plate comprising a first plurality of check valves configured to direct fluid in one direction in the second plurality of conduits. In some embodiments, the first plurality of check valves are arranged in a plurality of rows. In specific embodiments, the stack of plates comprises a second valve plate comprising a second plurality of check valves, and each check valve in the second plurality of check valves is in fluid communication with a row of the first plurality of check valves. In certain embodiments, the first plate is a first manifold plate and the second plate is a valve housing plate. In particular embodiments, the stack of plates comprises a first valve plate and a first channel plate, where the first valve plate is disposed between the first channel plate and the first manifold plate. In some embodiments, the stack of plates comprises a second manifold plate and a second valve plate, where the second manifold plate is disposed between the first channel plate and the second valve plate. In some embodiments, the stack of plates comprises a second channel plate, where the second channel plate is disposed between second valve plate and the valve housing plate.

In specific embodiments, the first manifold plate comprises: a first side and a second side, where the second side is opposite the first side; a first plurality of conduits configured to direct pressurized gas from the plurality of solenoid valves through the first manifold plate; and a second plurality of conduits between the first side and the second side, wherein each conduit in the second plurality of conduits is arranged at an acute angle to the first side.

In certain embodiments, the first channel plate comprises a first side and a second side, where the second side is opposite the first side; the first channel plate comprises a plurality of channels in the second side of the first channel plate; the first valve plate comprises a plurality of check valves arranged in a plurality of rows; each check valve in the first valve plate is aligned with a conduit of the second plurality of conduits in the first manifold plate; and each row of check valves in the first valve plate is aligned with a channel in the plurality of channels in the second side of the first channel plate. In particular embodiments, each check valve in the first valve plate is configured to direct fluid in one direction in a channel in the plurality of channels in the second side of the first channel plate. In some embodiments, each channel in the plurality of channels in the second side of the first channel plate comprises an exit port that extends through the first side of the first channel plate; and each check valve in a row of check valves of the first valve plate is configured to direct fluid toward the exit port of the channel to which the row of check valves is aligned.

In specific embodiments, the second manifold plate comprises a first side and a second side, wherein the second side is opposite the first side; the second manifold plate comprises a plurality of directional ports extending through the second manifold plate, where each directional port is arranged at an acute angle to the first side of the second manifold plate; and the exit port of each channel in the first channel plate is aligned with a directional port in the second manifold plate. In certain embodiments, the second valve plate comprises a plurality of check valves arranged in a row, and each directional port in the first channel plate is aligned with a check valve in the second valve plate.

In particular embodiments, the second channel plate comprises a first side and a second side, where the second side is opposite the first side; the second channel plate comprises an outlet channel in the second side of the second channel plate, where the outlet channel is aligned with the plurality of check valves of the second valve plate; the outlet channel of the channel valve plate comprises an outlet port; and each check valve in the second valve plate is configured to direct fluid toward the outlet port of the outlet channel.

In some embodiments, the outlet port of the second channel plate is aligned with a sample analysis port in the valve housing. In specific embodiments, the sample analysis port is in fluid communication with a flow cytometry analysis system. In certain embodiments, the plurality of gas valves are configured as solenoid valves. Particular embodiments further comprise a source of pressurized gas in fluid communication with the plurality of gas valves. In some embodiments, the source of pressurized gas comprises pressurized air. In specific embodiments, the source of pressurized gas comprises pressurized nitrogen. In certain embodiments, the first valve plate and the second valve plate are formed from a flexible polymer. In particular embodiments, the first valve plate and the second valve plate are formed from polytetrafluoroethylene (PTFE). In some embodiments, the first channel plate and the second channel plate are formed from polytetrafluoroethylene (PTFE).

Specific embodiments further comprise a control system configured to open and close the plurality of gas valves. In certain embodiments, the plurality of gas valves are arranged in a plurality of rows, the control system is configured to sequentially open and close each gas valve in an individual row of the plurality of rows. In particular embodiments, the control system is configured to sequentially open and close each valve in a first row of the plurality of rows, and the control system is configured to sequentially open and close each valve in a second row of the plurality of rows after each valve in the first row has been sequentially opened and closed. In certain embodiments, the first manifold plate comprises a first side and a second side, wherein the second side is opposite the first side; the second side of the first manifold plate is engaged with well plate comprising a plurality of wells, wherein each well comprises a sample; the plurality of gas valves are in fluid communication with a source of pressurized gas; and the pressurized gas directs a portion of each sample from a well in the plurality of wells when a gas valve is open.

In particular embodiments, the portion of each sample is directed from the well in the plurality of wells, through the first manifold plate, the first valve plate, the first channel plate, the second manifold plate, the second valve plate, the second channel plate and into the valve housing. In some embodiments, the first manifold plate comprises a first side and a second side, where the second side is opposite the first side; the first side of the first manifold plate is configured to engage the first valve plate; and the apparatus further comprises a plurality of sealing mechanisms coupled to the second side of the first manifold plate.

In certain embodiments, each sealing mechanism comprises an elastomeric o-ring. In particular each sealing mechanism comprises a plug disposed within the elastomeric o-ring, and the plug comprises a first conduit and a second conduit extending through the plug. In some embodiments, each sealing mechanism in the plurality of sealing mechanisms comprises: a collar comprising a tapered inner surface; a plug comprising a lower surface and a tapered outer surface, wherein the tapered outer surface of the plug is configured to engage the tapered inner surface of the collar; a first conduit extending through the plug; and a second conduit extending through the plug. Specific embodiments further comprise a disc coupled to the lower surface of the plug, wherein the first conduit and the second conduit extend through the disc.

In specific embodiments, each sealing mechanism in the plurality of sealing mechanisms comprises: a collar comprising a tapered inner surface and a tapered outer surface; a plug comprising a lower surface and a tapered outer surface, wherein the tapered outer surface of the plug is configured to engage the tapered inner surface of the collar; a disc coupled to the lower surface of the plug; a first conduit extending through the plug and the disc; and a second conduit extending through the plug and the disc. In certain embodiments, the disc and the tapered outer surface of the collar are configured to seal to a well in well plate. Particular embodiments further comprise a plate comprising a plurality of magnets.

Certain embodiments include an apparatus for sample acquisition and delivery, where the apparatus comprises: a first manifold plate, a first valve plate and a first channel plate, where the first valve plate is disposed between the first channel plate and the first manifold plate; a second manifold plate and a second valve plate, where the second manifold plate is disposed between the first channel plate and the second valve plate; a second channel plate and a valve housing, where the second channel plate is disposed between second valve plate and the valve housing. Particular embodiments include a plurality of gas valves disposed in the valve housing, where each gas valve is configured to allow gas to flow through the valve housing, the second channel plate, the second valve plate, the second manifold plate, the first channel plate, the first valve plate and the first manifold plate when each gas valve is in an open position.

In some embodiments, the first manifold plate comprises: a first side and a second side, where the first side is opposite the second side; a first plurality of conduits configured to direct pressurized gas from the plurality of solenoid valves through the first manifold plate; and a second plurality of conduits between the second side and the first side, wherein each conduit in the second plurality of conduits is arranged at an acute angle to the first side. In specific embodiments, the first channel plate comprises a first side and a second side, wherein the second side is opposite the first side; the first channel plate comprises a plurality of channels in the second side of the first channel plate; the first valve plate comprises a plurality of check valves arranged in a plurality of rows; each check valve in the first valve plate is aligned with a conduit of the second plurality of conduits in the first manifold plate; and each row of check valves in the first valve plate is aligned with a channel in the plurality of channels in the second side of the first channel plate.

In certain embodiments, each check valve in the first valve plate is configured to direct fluid in one direction in a channel in the plurality of channels in the second side of the first channel plate. In particular embodiments, each channel in the plurality of channels in the second side of the first channel plate comprises an exit port that extends through the first side of the first channel plate; and each check valve in a row of check valves of the first valve plate is configured to direct fluid toward the exit port of the channel to which the row of check valves is aligned. In some embodiments, the second manifold plate comprises a first side and a second side, wherein the second side is opposite the first side; the second manifold plate comprises a plurality of directional ports extending through the second manifold plate, wherein each directional port is arranged at an acute angle to the first side of the second manifold plate; and the exit port of each channel in the first channel plate is aligned with a directional port in the second manifold plate. In specific embodiments, the second valve plate comprises a plurality of check valves arranged in a row; and each directional port in the first channel plate is aligned with a check valve in the second valve plate.

In particular embodiments, the second channel plate comprises a first side and a second side; the second channel plate comprises an outlet channel in the second side of the second channel plate, where the outlet channel is aligned with the plurality of check valves of the second valve plate; the outlet channel of the channel valve plate comprises an outlet port; and each check valve in the second valve plate is configured to direct fluid toward the outlet port of the outlet channel. In some embodiments, the outlet port of the second channel plate is aligned with a sample analysis port in the valve housing. In specific embodiments, the sample analysis port is in fluid communication with a flow cytometry analysis system. In certain embodiments, the plurality of gas valves are configured as solenoid valves. Particular embodiments, further comprise a source of pressurized gas in fluid communication with the plurality of gas valves. In some embodiments, the source of pressurized gas comprises pressurized air or pressurized nitrogen. In specific embodiments, the first valve plate and the second valve plate are formed from a flexible polymer.

In certain embodiments, the first valve plate and the second valve plate are formed from polytetrafluoroethylene (PTFE), and in particular embodiments the first channel plate and the second channel plate are formed from polytetrafluoroethylene (PTFE). Some embodiments further comprise a control system configured to open and close the plurality of gas valves. In specific embodiments, the plurality of gas valves are arranged in a plurality of rows; and the control system is configured to sequentially open and close each gas valve in an individual row of the plurality of rows. In certain embodiments, the control system is configured to sequentially open and close each valve in a first row of the plurality of rows, and the control system is configured to sequentially open and close each valve in a second row of the plurality of rows after each valve in the first row has been sequentially opened and closed.

In particular embodiments, the first manifold plate comprises a first side and a second side; the second side of the first manifold plate is engaged with well plate comprising a plurality of wells, where each well comprises a sample; the plurality of gas valves are in fluid communication with a source of pressurized gas; and the pressurized gas directs a portion of each sample from a well in the plurality of wells when a gas valve is open. In some embodiments, the portion of each sample is directed from the well in the plurality of wells, through the first manifold plate, the first valve plate, the first channel plate, the second manifold plate, the second valve plate, the second channel plate and into the valve housing. In specific embodiments, the first manifold plate comprises a first side and a second side; the first side of the first manifold plate is configured to engage the first valve plate; and the apparatus further comprises a plurality of sealing mechanisms coupled to the second side of the first manifold plate.

In certain embodiments, each sealing mechanism comprises an elastomeric o-ring. In particular each sealing mechanism comprises a plug disposed within the elastomeric o-ring, and the plug comprises a first conduit and a second conduit extending through the plug. In some embodiments, each sealing mechanism in the plurality of sealing mechanisms comprises: a collar comprising a tapered inner surface; a plug comprising a lower surface and a tapered outer surface, wherein the tapered outer surface of the plug is configured to engage the tapered inner surface of the collar; a first conduit extending through the plug; and a second conduit extending through the plug. Specific embodiments further comprise a disc coupled to the lower surface of the plug, wherein the first conduit and the second conduit extend through the disc.

In certain embodiments, each sealing mechanism in the plurality of sealing mechanisms comprises: a collar comprising a tapered inner surface and a tapered outer surface; a plug comprising a lower surface and a tapered outer surface, wherein the tapered outer surface of the plug is configured to engage the tapered inner surface of the collar; a disc coupled to the lower surface of the plug; a first conduit extending through the plug and the disc; and a second conduit extending through the plug and the disc. In particular embodiments, the disc and the tapered outer surface of the collar are configured to seal to a well in well plate. Some embodiments further comprise a plate comprising a plurality of magnets.

Certain embodiments include a method of obtaining a plurality of samples for flow cytometry analysis, where the method comprises: positioning a sample acquisition apparatus above a well plate comprising a plurality of wells; and sequentially directing a flow of gas from the sample acquisition apparatus into each well in the plurality of wells, where the flow of gas from the sample acquisition apparatus into each well displaces a portion of a sample from each well in the plurality of wells into the sample acquisition apparatus, and where the sample acquisition apparatus does not move relative to the well plate. In particular embodiments, each portion of the sample from each well in the plurality of wells directed into the sample acquisition apparatus is separated by a volume of gas from the flow of gas. In some embodiments, the sample acquisition apparatus comprises: a plurality of plates; and a plurality of valves configured to allow the flow of gas to pass through the plurality of plates, wherein each valve in the plurality of valves is in fluid communication with a well in the plurality of wells. In specific embodiments, each valve of the plurality of valves is initially in the closed position; and sequentially directing the flow of gas from the sample acquisition apparatus into each well in the plurality of wells comprises sequentially opening and closing the plurality of valves.

In certain embodiments, the plurality of valves are arranged in a plurality of rows, and sequentially opening and closing the plurality of valves comprises: opening and closing a first valve in a first row in the plurality of valves; opening and closing a second valve in the first row of the plurality of valves after the first valve has been opened and closed, wherein the second valve is adjacent to the first valve; and opening and closing each valve in the first row, wherein each valve is opened and closed after an adjacent valve has been opened and closed. Particular embodiments include: sequentially opening and closing the plurality of valves further comprises: opening and closing a first valve in a second row in the plurality of valves; opening and closing a second valve in the second row of the plurality of valves after the first valve has been opened and closed, wherein the second valve is adjacent to the first valve; and opening and closing each valve in the second row, wherein each valve is opened and closed after an adjacent valve has been opened and closed.

Specific embodiments include a flow cytometry system comprising: a cuvette; a sample acquisition apparatus comprising a plurality of gas valves, wherein the sample acquisition apparatus comprises a sample port in fluid communication with the cuvette; a gas manifold system in fluid communication with the plurality of gas valves; a control system configured to sequentially open and close each gas valve in the plurality of gas valves; a sheath fluid supply system in fluid communication with the cuvette; and a drain manifold in fluid communication with the cuvette. In certain embodiments, the sample port is in fluid communication with the cuvette via a sample conduit, and the flow cytometry system further comprises a bubble detector configured to detect a bubble in the sample conduit. Particular embodiments further comprise a magnet configured to move relative to the sample conduit. In some embodiments, the sheath fluid supply system and the drain manifold are in fluid communication with a probe bath.

Specific embodiments include a flow cytometry system comprising: a cuvette; a water supply; a sample proportional valve; a sheath proportional valve; a sample acquisition apparatus, wherein the sample acquisition apparatus comprises a sample port in fluid communication with the cuvette, wherein the sample proportional valve is in fluid communication with the sample acquisition apparatus and the water source; a sheath fluid supply system in fluid communication with the cuvette, wherein the sheath proportional valve is in fluid communication with the sheath fluid supply system and the water source; and a drain manifold in fluid communication with the cuvette.

Certain embodiments include an apparatus for acquiring liquid samples from a multiwell plate, the apparatus comprising: a first manifold plate having a first side and a second side, wherein the second side is opposite the first side; a plurality of first conduits extending from the first side to the second side of the first manifold plate and a plurality of second conduits extending from the first side to the second side of the first manifold plate, wherein the plurality of first conduits and the plurality of second conduits are configured such that when the first side of the first manifold plate is positioned adjacent a multiwell plate each well of the multiwell plate is in fluid communication with one of the plurality of first conduits and one of the plurality of second conduits; a plurality of gas valves in fluid communication with the plurality of first conduits; and a sample outlet port in fluid communication with the plurality of second conduits. In particular embodiments, the multiwell plate is 96-well plate and the plurality of first conduits comprises 96 first conduits, the plurality of second conduits comprises 96 second conduits, and the plurality of gas valves comprises 96 gas valves. In some embodiments, the multiwell plate is 384-well plate and the plurality of first conduits comprises 384 first conduits, the plurality of second conduits comprises 384 second conduits, and the plurality of gas valves comprises 384 gas valves. Specific embodiments, further comprise a pressurized gas reservoir, wherein the pressurized gas reservoir is in fluid communication with the plurality of gas valves and is selectively in fluid communication with the plurality of the plurality of first conduits via the plurality of gas valves.

Certain embodiments further comprise a plurality of protrusions coupled to the first side of the first manifold plate and configured to insert at least partially into the wells of the multiwell plate to create a substantially airtight seal between each well and the first and second conduits in fluid communication with each well. In particular embodiments, the plurality of protrusions each comprise an obturating ring. In some embodiments, each of the first conduits are positioned at a first angle to the first manifold plate; and each of the second conduits are positioned at a second angle to the first manifold plate. In specific embodiments, the first angle is approximately 90 degrees and the second angle is approximately 45 degrees.

Certain embodiments include an air valve housing plate having a first side and a second side, where the second side is opposite the first side, and where the plurality of air valves are coupled to the first side of the air valve housing plate; a third plurality of conduits extending from the first side of the air valve housing plate to the second side of the air valve housing plate, wherein the plurality of air valves are in fluid communication with the plurality of first conduits in the sample manifold plate via the plurality of third conduits. Particular embodiments further comprise: a first channel plate; and a second channel plate, where the first channel plate is disposed between the first manifold plate and the plurality of gas valves, and where the second channel plate is disposed between the first channel plate and the plurality of gas valves. Specific embodiments further comprise: a first valve plate and a second valve plate, where: the first valve plate is disposed between the first manifold plate and the first channel plate; and the second valve plate is disposed between the first channel plate and the second channel plate.

The term "coupled" is defined as connected, although not necessarily directly, and not necessarily mechanically. Two items are "coupleable" if they can be coupled to each other, and, when coupled, may still be characterized as "coupleable." Unless the context explicitly requires otherwise, items that are coupleable are also decoupleable, and vice-versa. One non-limiting way in which a first structure is coupleable to a second structure is for the first structure to be configured to be coupled (or configured to be coupleable) to the second structure.

The terms "a" and "an" are defined as one or more unless this disclosure explicitly requires otherwise.

The term "substantially" and its variations (e.g., "approximately" and "about") are defined as being largely but not necessarily wholly what is specified (and include wholly what is specified) as understood by one of ordinary skill in the art. In any disclosed embodiment, the terms "substantially," "approximately," and "about" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements possesses those one or more steps or elements, but is not limited to possessing only those one or more elements. Likewise, a step of a method or an element of a device that "comprises," "has," "includes" or "contains" one or more features possesses those one or more features, but is not limited to possessing only those one or more features. For example, a system that comprises four channels may have more than four channels.

Furthermore, a device or structure that is configured in a certain way is configured in at least that way, but may also be configured in ways that are not listed. Metric units may be derived from the English units provided by applying a conversion and rounding to the nearest millimeter.

The feature or features of one embodiment may be applied to other embodiments, even though not described or illustrated, unless expressly prohibited by this disclosure or the nature of the embodiments.

Any embodiment of any of the disclosed devices and methods can consist of or consist essentially of—rather than comprise/include/contain/have—any of the described elements and/or features and/or steps. Thus, in any of the claims, the term "consisting of" or "consisting essentially of" can be substituted for any of the open-ended linking verbs recited above, in order to change the scope of a given claim from what it would otherwise be using the open-ended linking verb.

Other features and associated advantages will become apparent with reference to the following detailed description of specific embodiments in connection with the accompanying drawings.

BRIEF DESCRIPTION OF THE DRAWINGS

The following drawings illustrate by way of example and not limitation. For the sake of brevity and clarity, every feature of a given structure may not be labeled in every figure in which that structure appears. Identical reference numbers do not necessarily indicate an identical structure. Rather, the same reference number may be used to indicate a similar feature or a feature with similar functionality, as may non-identical reference numbers.

DETAILED DESCRIPTION

Various features and advantageous details are explained more fully with reference to the non-limiting embodiments that are illustrated in the accompanying drawings and detailed in the following description. It should be understood, however, that the detailed description and the specific examples, while indicating embodiments of the invention, are given by way of illustration only, and not by way of limitation. Various substitutions, modifications, additions, and/or rearrangements will become apparent to those of ordinary skill in the art from this disclosure.

In the following description, numerous specific details are provided to provide a thorough understanding of the disclosed embodiments. One of ordinary skill in the relevant art will recognize, however, that the invention may be practiced without one or more of the specific details, or with other methods, components, materials, and so forth. In other instances, well-known structures, materials, or operations are not shown or described in detail to avoid obscuring aspects of the invention. It is understood that for purposes of clarity, not all reference numbers are shown for every component visible in each figure.

It should be understood that the present devices and methods are not intended to be limited to the particular forms disclosed. Rather, they are to cover all modifications, equivalents, and alternatives falling within the scope of the claims.

Figure 1:
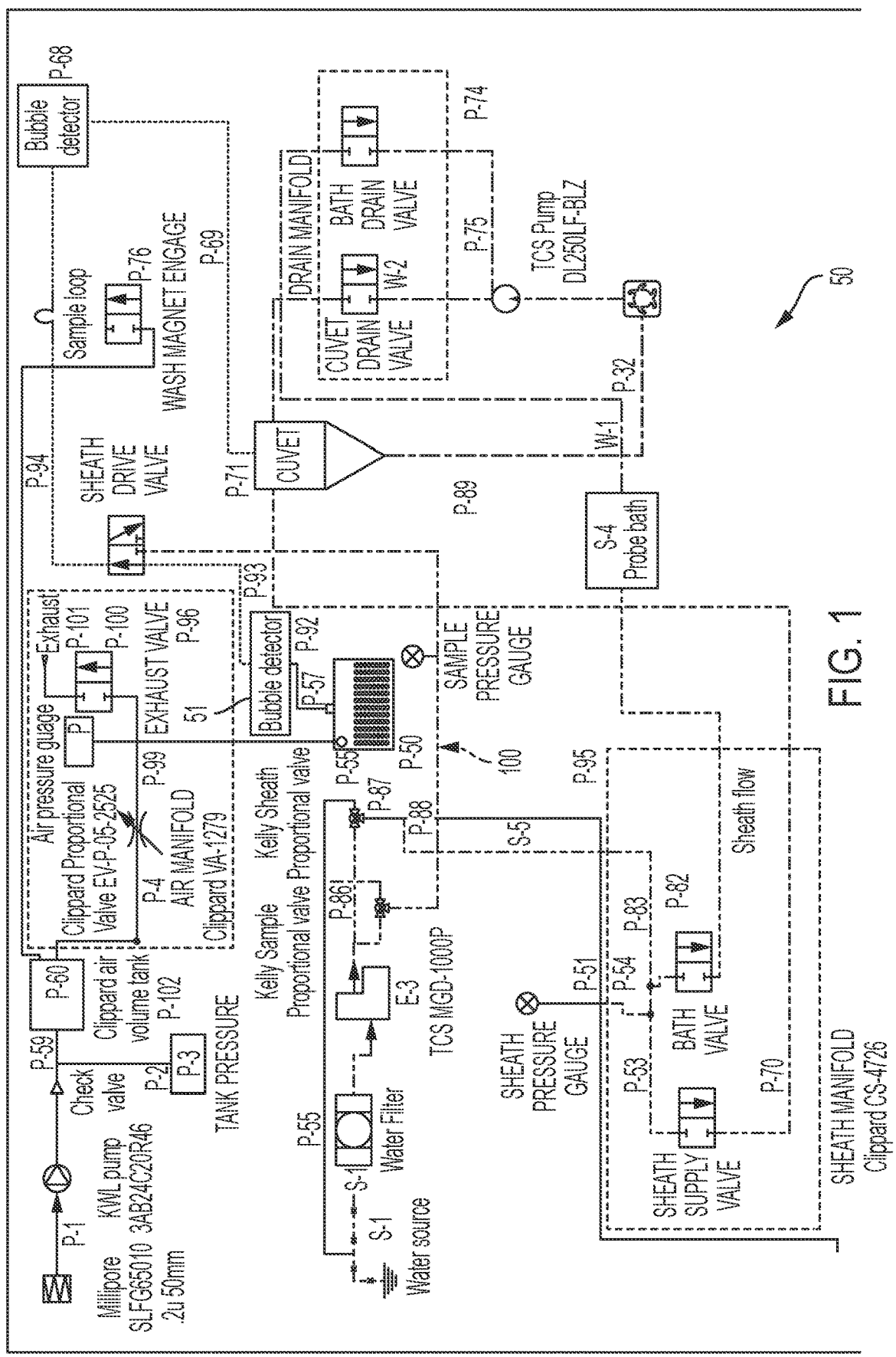
FIG. 1 is a schematic of a schematic diagram for a flow cytometry system comprising an apparatus configured for sample acquisition and delivery.

Referring initially to FIG. 1, a schematic diagram for a flow cytometry system 50 comprises an apparatus 100 configured for sample acquisition and delivery.

An overview of the operation of apparatus 100 will be presented initially, followed by further discussion of individual components. In general, apparatus 100 can rapidly acquire samples from a plurality of reservoirs, including for example, wells in a well plate. As used herein, the term "sample" or "sample fluid" is intended to be interpreted broadly to include a portion (including all) of a volume of matter comprising liquid contained in a reservoir. Apparatus 100 can be incorporated in a flow cytometry system to provide for rapid sample analysis.

Apparatus 100 includes a stack of plates that can be coupled to a well plate and individually seal each well in the well plate. As used herein, the terms "plate" and "plates" is intended to be construed broadly, and refers to any generally planar structure without limiting to a particular shape, thickness, or rigidity. For example, certain components in the disclosed apparatus may be referred to as "valve plates", which may be formed from sheets of flexible (e.g. polymeric) material.

Apparatus 100 also includes a first set of conduits that extend from a set of valves, through the plates and into each well. Each valve is coupled to a pressurized gas supply, so that as each valve is opened, pressurized gas is directed into a well. In particular embodiments, the valves may be solenoid valves. The pressurized gas directs fluid from each well into a second set of conduits that extend through the stack of plates and to a sample port for analysis by the flow cytometry system. The valves can be sequentially opened and closed to provide efficient sample acquisition and delivery for analysis. Exemplary embodiments are not limited to the orientation shown in the figures. For ease of understanding the operation of apparatus 100, with respect to the included figures the gas is directed downward through the apparatus, while the sample fluid is directed upward from the sample container (e.g. well) to the sample port. It is understood the "downward" and "upward" description is only for purpose of explanation with respect to the attached figures and is not intended to limit exemplary embodiments to any particular orientation.

Unlike typical existing systems, apparatus 100 does not include a pipette or other component that must be indexed to individual wells to aspirate a sample. Apparatus 100 therefore includes fewer components that move relative to a well plate from which samples are acquired. As explained in more detail below, apparatus 100 comprises angled conduits and thin plates of flexible material that include check valves to direct sample flow from the wells to the sample port.

Referring now to FIGS. 2-5, apparatus 100 includes a stacked assembly of plates comprising (from bottom to top) a first manifold plate 110, a first valve plate 120, a first channel plate 130, a second manifold plate 140, a second valve plate 150, a second channel plate 160, and a valve housing 170. In this embodiment, valve housing 170 comprises a first valve housing plate 180 and a second valve housing plate 190. For purposes of clarity, certain components of apparatus 100 are not shown or labeled in each in the assembly and exploded views, but included in the section views discussed further below.

Figure 2:
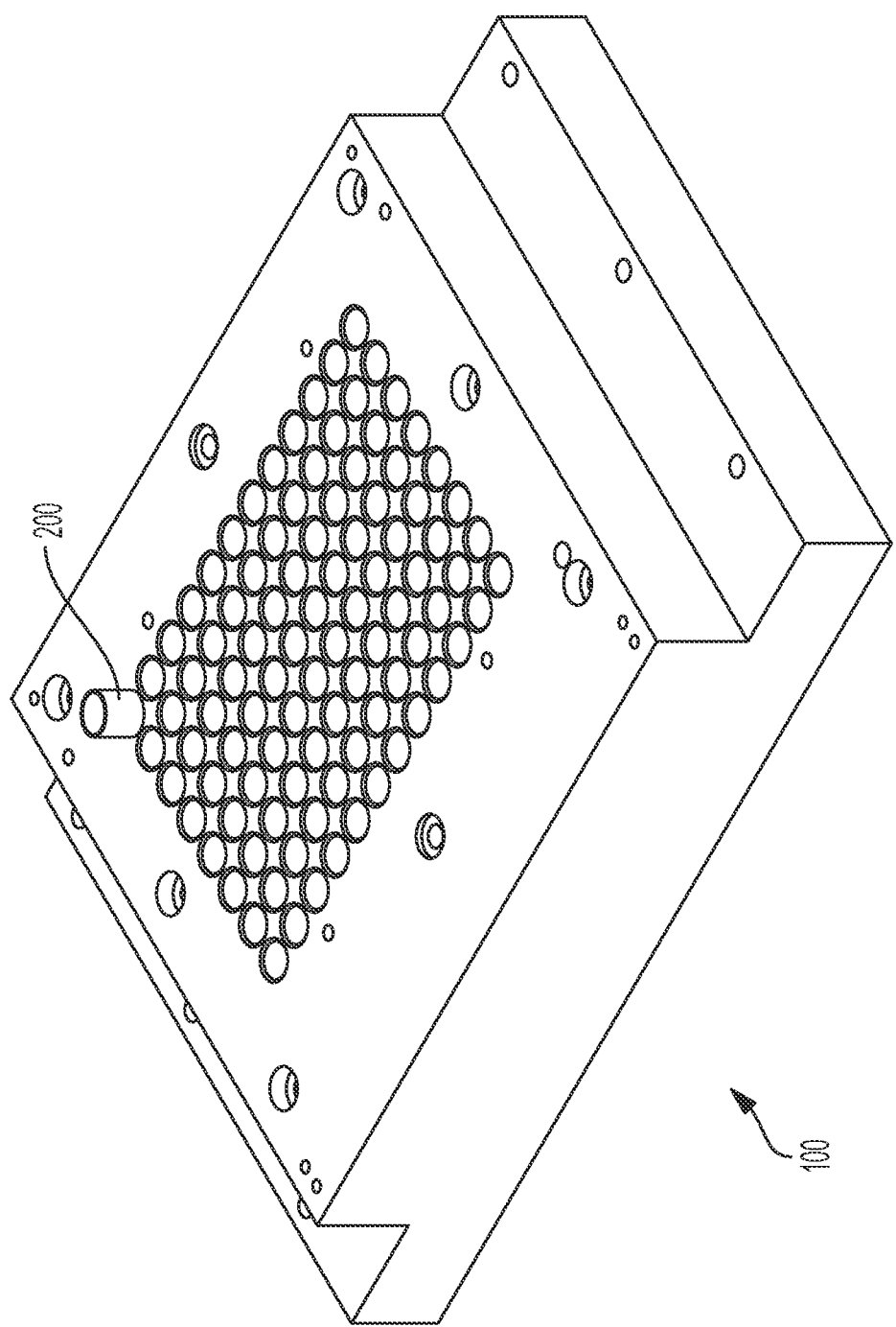
FIG. 2 is a perspective view of an apparatus for acquiring samples according to an exemplary embodiment.
Figure 3:
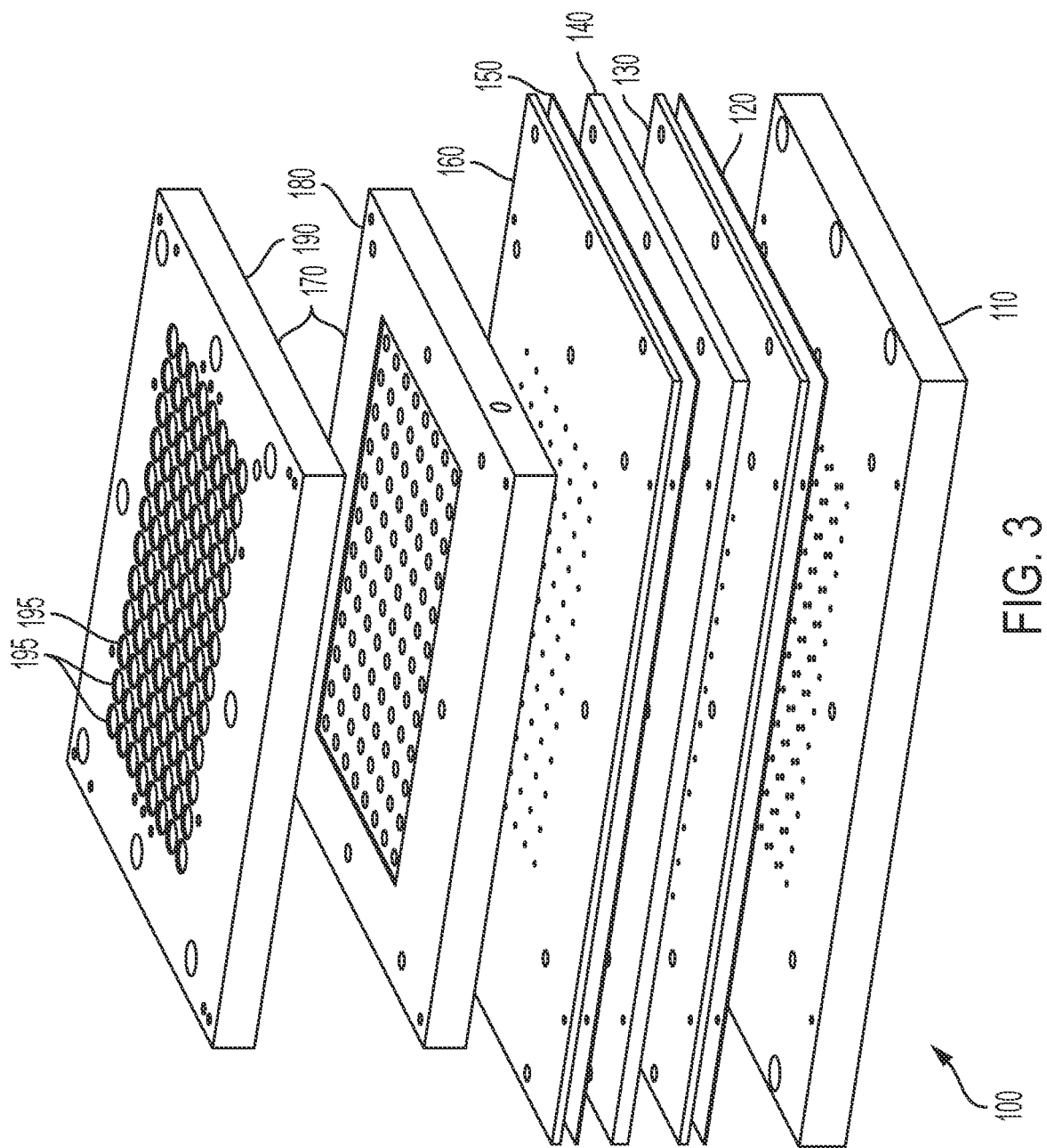
FIG. 3 is an exploded view of the embodiment of FIG. 1.
Figure 4:
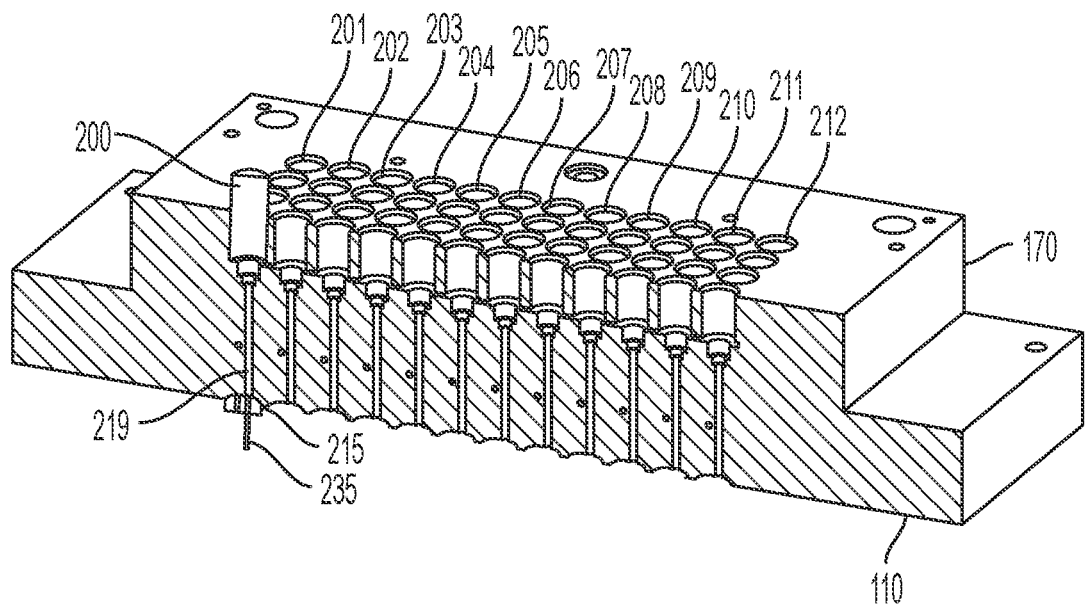
FIG. 4 is a first section view of the embodiment of FIG. 1.
Figure 5:
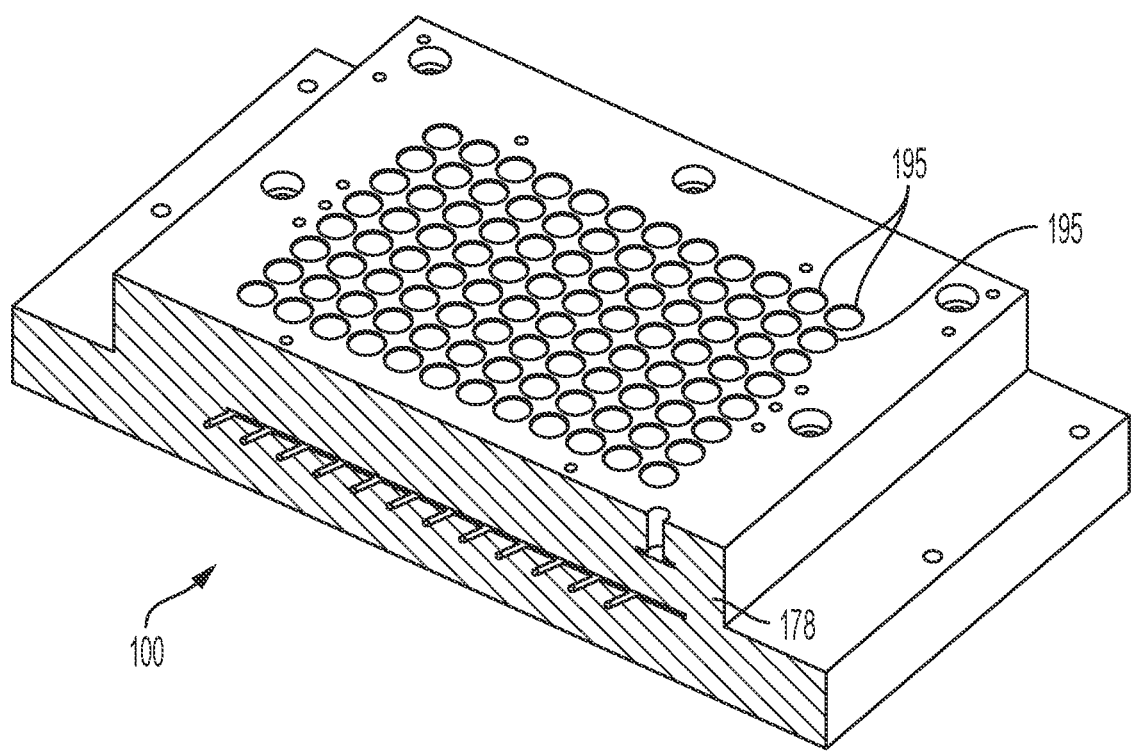
FIG. 5 is a second section view of the embodiment of FIG. 1.

During operation of apparatus 100, pressurized gas (e.g. air or nitrogen) is directed to a gas valve 200 that can be controlled to open and allow the gas to flow through conduits 219 into a well in a well plate. For purposes of clarity, only a single gas valve 200 is shown in FIGS. 2 and 4. It is understood that each aperture 195 in second valve housing plate 190 may comprise a gas valve 200. In the embodiment shown, second valve housing plate 190 comprises apertures 195 in an arrangement of twelve rows 201-212 of eight apertures each that are configured to correspond with a 96 well plate. It is understood that other embodiments may comprise other arrangements, including for example, a 384 well plate.

Figure 6:
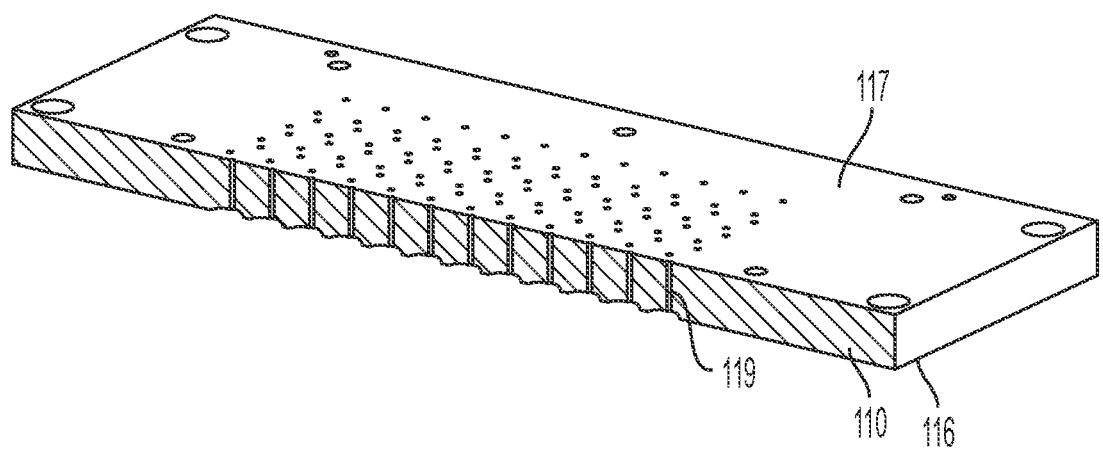
FIG. 6 is a first section view of a first manifold plate of the embodiment of FIG. 1.
Figure 9:
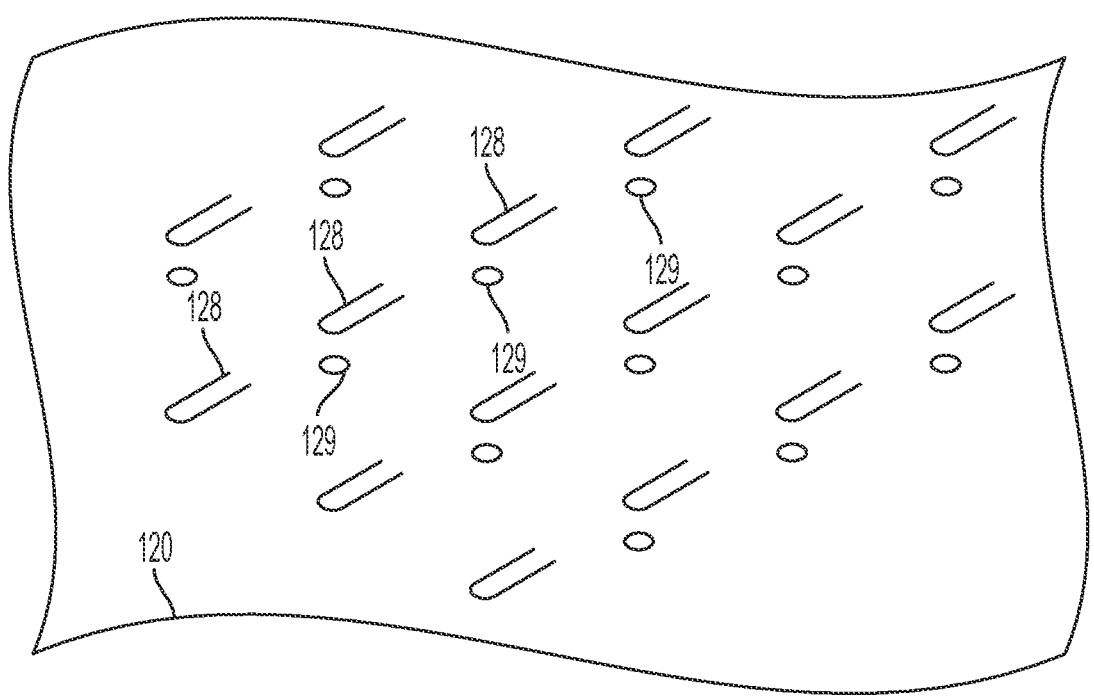
FIG. 9 is a more detailed view of the first valve plate of FIG. 8.
Figure 12:
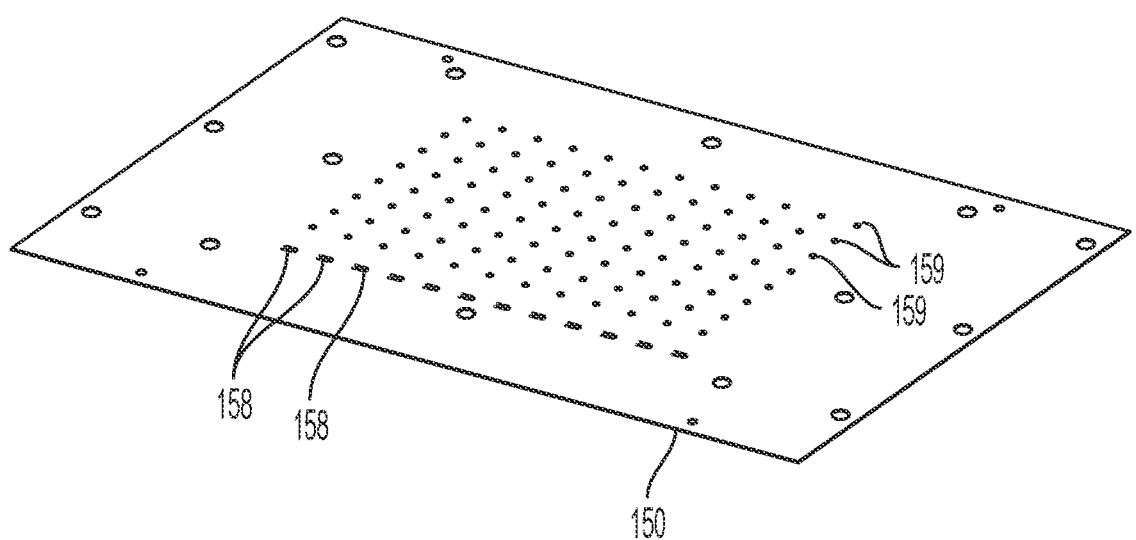
FIG. 12 is a perspective view of a second valve plate of the embodiment of FIG. 1.
Figure 13:
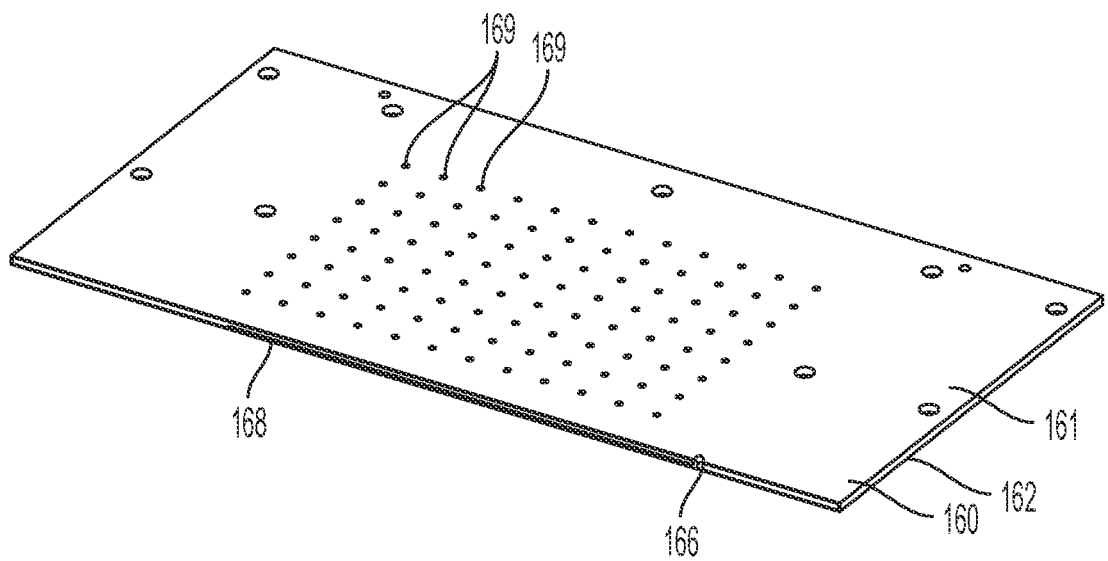
FIG. 13 is a section view of a second channel plate of the embodiment of FIG. 1
Figure 14:
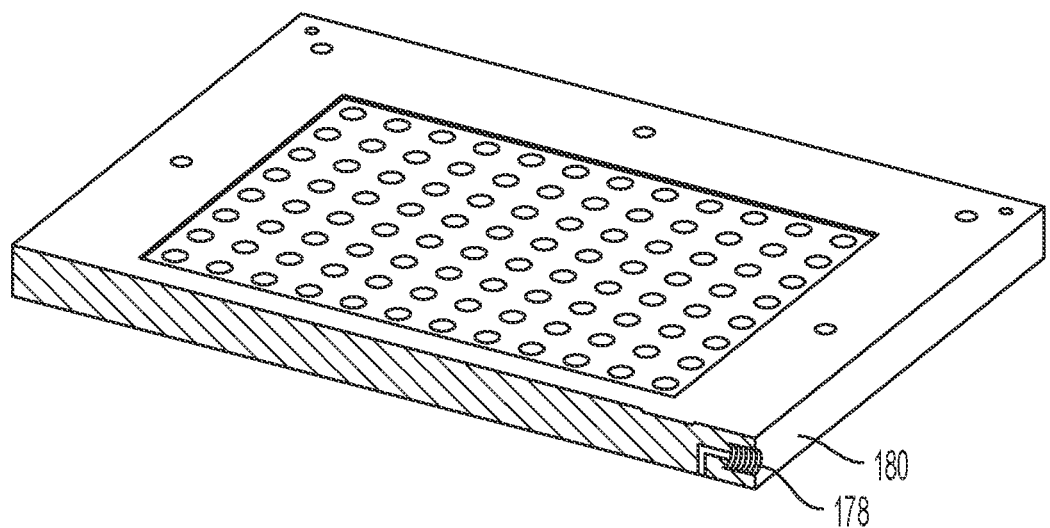
FIG. 14 is a first section view of first valve housing plate of the embodiment of FIG. 1.
Figure 15:
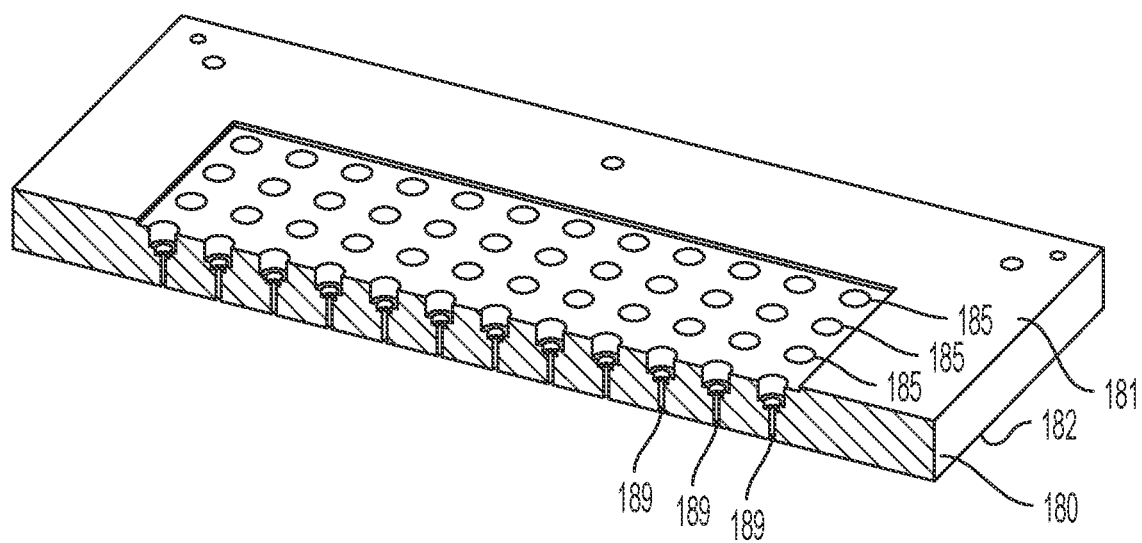
FIG. 15 is a second section view of first valve housing plate of the embodiment of FIG. 1
Figure 16:
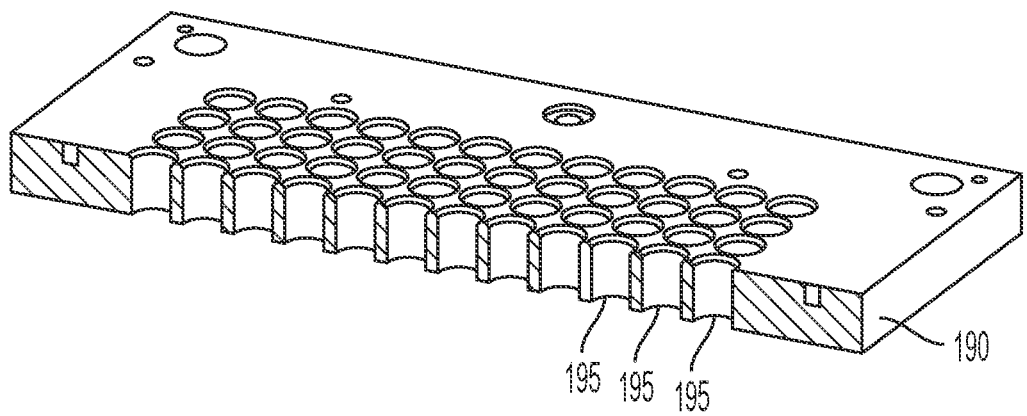
FIG. 16 is a section view of second valve housing plate of the embodiment of FIG. 1.

In the embodiment shown, each conduit 219 comprises a plurality of apertures or conduits in each of the plates in apparatus 100 and includes a tube 235 that extends into each sample container (e.g. well). In the illustrated embodiment, each conduit 219 comprises conduit 119 in first manifold plate 110 (shown in FIG. 6), aperture 129 in first valve plate 120 (FIG. 9), aperture 139 in first channel plate 130 (FIG. 10), aperture 149 in second manifold plate 140 (FIG. 11), aperture 159 in second valve plate 150 (FIG. 12), aperture 169 in second channel plate 160 (FIG. 13), and conduit 189 in first valve housing plate 180 (FIG. 15). As shown in FIG. 15, first air valve housing plate 180 comprises apertures 185 extending between a first side 181 and a second side 182 that is opposite of first side 181. Air valves 200 can extend through second air valve housing plate 170 and be coupled to first side 181 of first valve housing plate 180. Air valves 200 are in fluid communication with conduits 119 in first manifold plate 110 via conduits 189 in first valve housing plate 180 (and additional conduits and apertures in the plates as described above).

Figure 7:
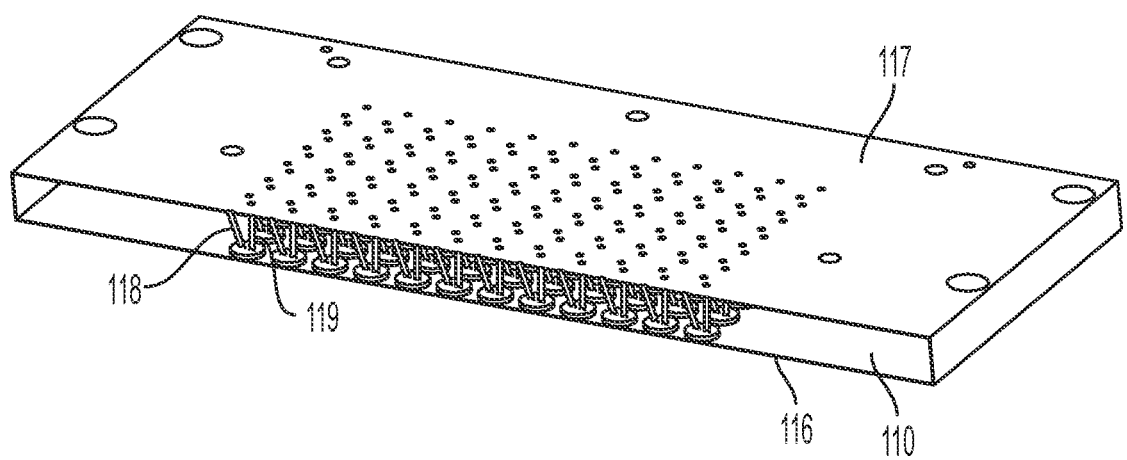
FIG. 7 is a second section view of a first manifold plate of the embodiment of FIG. 1.
Figure 8:
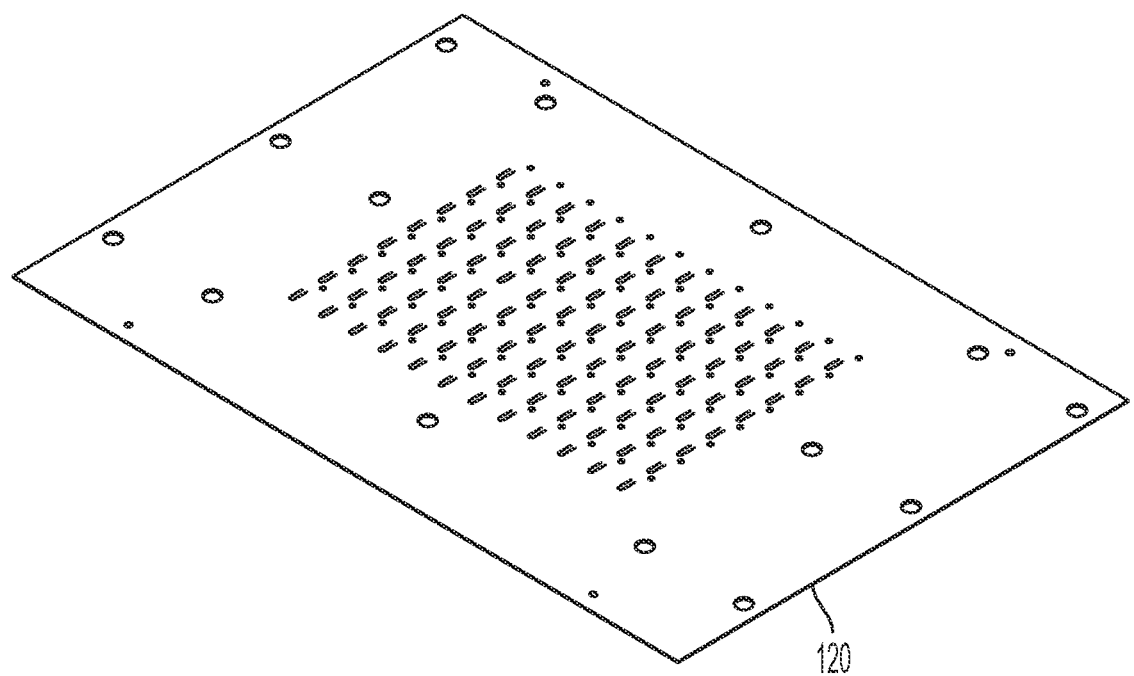
FIG. 8 is a perspective view of a first valve plate of the embodiment of FIG. 1.
Figure 17:
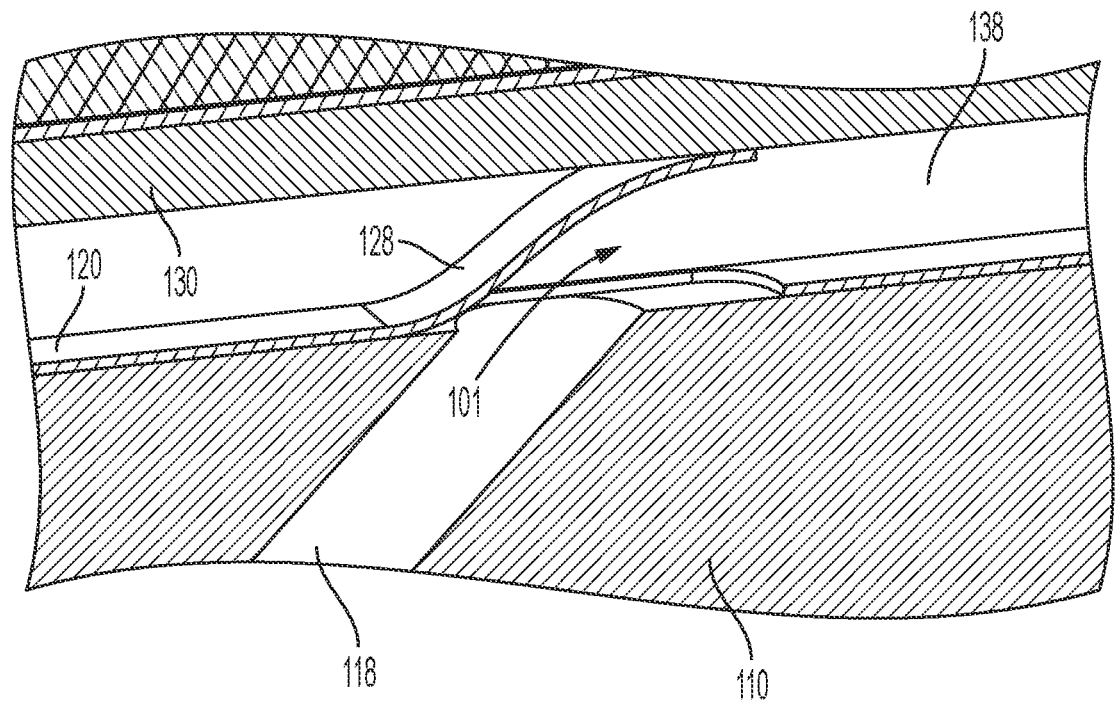
FIG. 17 is a detailed view of the first valve plate of FIGS. 8 and 9 during operation.

The pressurized gas from each gas valve 200 is directed through a conduit 213 and forces the sample fluid from the well into an angled conduit 118 in first manifold plate (also referred to as a sample manifold plate) 110 as shown in FIG. 7. First manifold plate comprises a first side 116 opposite a second side 117, and each of the plurality of angled conduits 118 is arranged at an acute angle to first side 116. The sample fluid exits angled conduit 118 and passes through valves 128 in first valve plate 120 shown in FIGS. 8 and 9 (a more detailed view of valve 128 during operation is shown in FIG. 17). As shown in FIG. 17, valve 128 is lifted by the sample fluid flow (indicated by arrow 101) such that valve 128 seals against first channel plate 130. In the configuration shown, first valve plate 120 is located between first manifold plate 110 and first channel plate 130.

Figure 10:
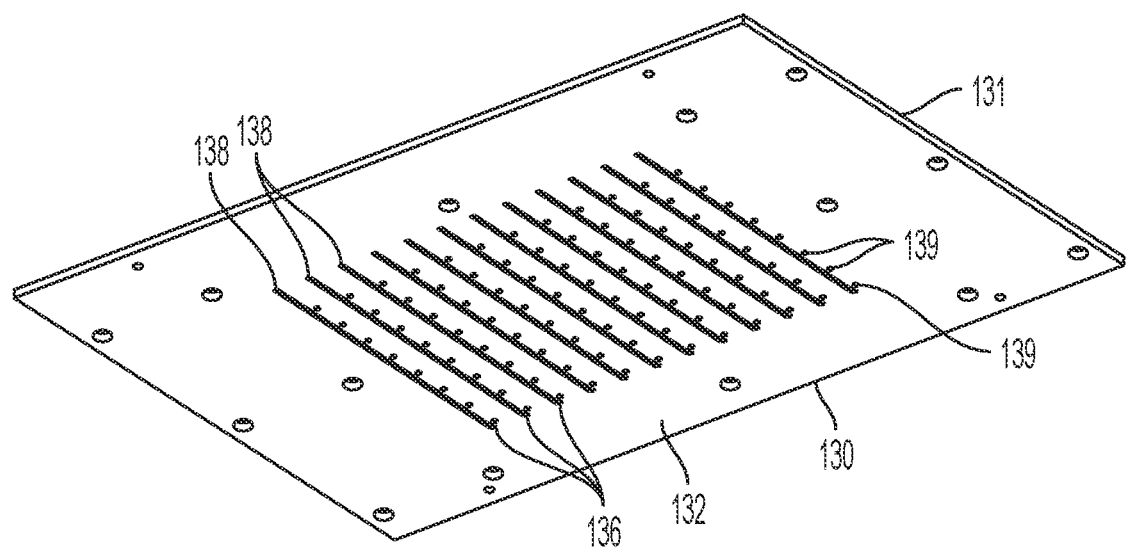
FIG. 10 is a perspective view of a first channel plate of the embodiment of FIG. 1.

After passing through valves 128 in first valve plate 120, the sample fluid is directed to channels 138 formed in a second side 132 of first channel plate 130 shown in FIG. 10. Channels 138 do not extend completely through first channel plate 130, but channels 138 are in fluid communication with an exit port or conduit 136 that extends from second side 132 of channel plate 130 to a first side 131 of first channel plate 130 that is opposite of second side 132. When apparatus 100 is assembled, angled conduits 118 in first manifold plate 110 are angled toward conduits 136 shown in FIG. 10. This angled configuration (along with the flap configuration of valve 128) allows sample fluid flow to pass through valves 128 and toward conduits 136 without back flowing through channel 138 (e.g. flowing away from conduits 136).

Figure 11:
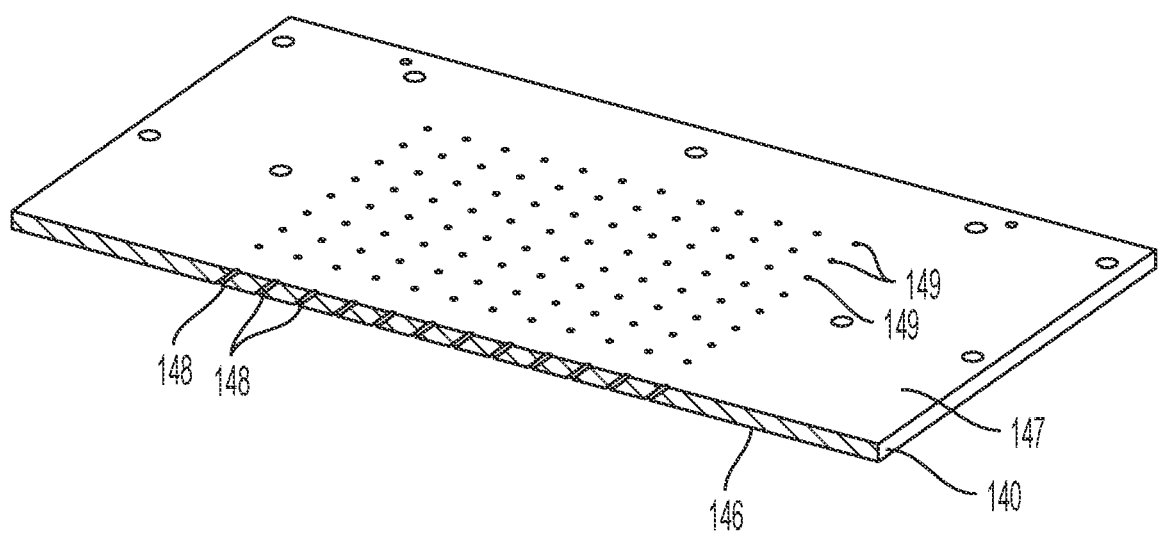
FIG. 11 is section view of a second manifold plate of the embodiment of FIG. 1

After exiting conduits 136 from first channel plate 130, the sample fluid is directed through directional ports or conduits 148 through second manifold plate 140 shown in FIG. 11. Second manifold plate comprises a first side 146 opposite a second side 147, and each of the plurality of angled conduits 148 is arranged at an acute angle to first side 146. Similar to angled conduits 118, conduits 148 are also angled to direct the sample fluid in the desired direction. From conduits 148, the sample fluid then passes through valves 158 in second valve plate 150 shown in FIG. 12. Valves 158 are configured similar to valves 128 and allow the sample fluid to pass into an outlet or cross flow channel 168 in second channel plate 160 in the desired direction (e.g. toward an outlet port or conduit 166). Cross flow channel 168 is in fluid communication with conduit 166 that extends from a second side 162 of second channel plate 160 to a first side 161 of second channel plate 160. Conduit 166 is in further fluid communication with a sample port 178 in first valve housing plate 180 of valve housing 170. In certain embodiments, sample port 178 can be accessed by a flow cytometry system for analysis of the sample fluid.

Figure 18:
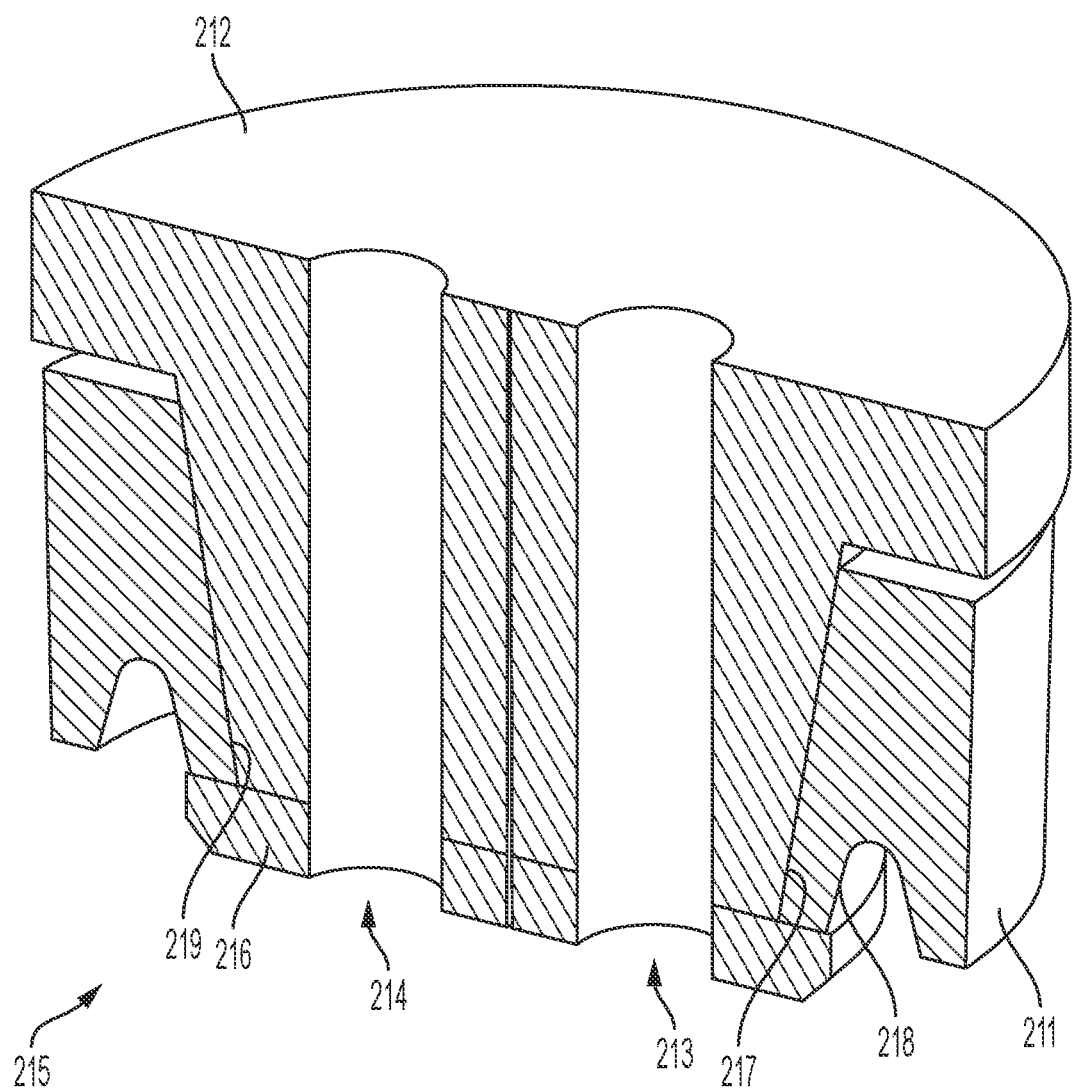
FIG. 18 is a section view of a sealing mechanism of the embodiment of FIG. 1.

Referring now to FIG. 18, exemplary embodiments may comprise a scaling mechanism 215 configured to seal apparatus 100 (in particular first manifold plate 110) to a sample container, including for example, a well in a well plate. In the embodiment shown, sealing mechanism 215 comprises a collar or obturating ring 211 surrounding a plug or central portion 212. Sealing mechanism 215 can further comprise a disc 216 that can be coupled to first manifold plate 110 (as shown in FIG. 4). Other embodiments may comprise a scaling mechanism configured as a gasket with openings corresponding to wells in a well plate.

In specific embodiments, obturating ring may be formed from a softer material than central portion 112. Central portion 212 can comprise a conduit 213 configured to allow pressurized gas to pass into a sample container (e.g. a sample well). Central portion 212 can also comprise a conduit 214 configured to allow sample fluid to pass from the sample container to angled conduit 118 in first manifold plate 110. Ring 211 can comprise a tapered inner surface 217 and a tapered outer surface 218, while central portion 212 comprises a tapered outer surface 219 configured to engage tapered inner surface 217 of ring 211. During operation of apparatus 100, sealing mechanism 215 can effectively seal apparatus 100 to allow pressurized gas to direct sample fluid from a sample container and into apparatus 100.

Exemplary embodiments of the present disclosure provide significant benefits over typical sample acquisition apparatus and methods. For example, exemplary embodiments can reduce the sample acquisition time, which can reduce the time and costs associated with sample preparation processes. This is particularly true of processes that include a high number of cycles, including for example, flow cytometry processes.

In particular embodiments, apparatus 100 can be operated such that each valve 200 in a particular row of valves is sequentially opened and closed prior to operating valves from any other rows. In a specific embodiment, each valve 200 in a first row is sequentially opened, followed by each valve 200 in a second row being sequentially opened, until each valve 200 in each row has been sequentially opened. By following a known pattern of valve operation, the order of the acquired samples can also be determined.

In some embodiments, each gas valve 200 may be opened for a period of time sufficient to evacuate the entire sample from the sample container and to introduce a gas bubble into angled conduit 118 (and the subsequent conduits and channels through which the sample fluid flows). Accordingly, a gas bubble can separate each sample evacuated from a particular sample container. In specific embodiments, flow cytometry system 50 may comprise a bubble detector 51 to detect a bubble between different samples. Apparatus 100 can therefore allow samples from multiple sample containers to be distinguished quickly and accurately without having to move an aspirating needle to each sample container to remove the sample.

The above specification and examples provide a complete description of the structure and use of an exemplary embodiment. Although certain embodiments have been described above with a certain degree of particularity, or with reference to one or more individual embodiments, those skilled in the art could make numerous alterations to the disclosed embodiments without departing from the scope of this invention. As such, the illustrative embodiment of the present devices is not intended to be limited to the particular forms disclosed. Rather, they include all modifications and alternatives falling within the scope of the claims, and embodiments other than the one shown may include some or all of the features of the depicted embodiment. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not to be interpreted as including means-plus- or step-plus-function limitations, unless such a limitation is explicitly recited in a given claim using the phrase(s) "means for" or "step for," respectively.

REFERENCES

The following references are incorporated herein by reference:
U.S. Pat. No. 5,560,811
U.S. Pat. No. 6,042,709
U.S. Pat. No. 6,149,787
U.S. Pat. No. 7,024,281
U.S. Pat. Pub. 2004/0071602
U.S. Pat. Pub. 2005/0238545
U.S. Pat. Pub. 2006/0198765
U.S. Pat. Pub. 2017/0199210

We claim:

1. A method of obtaining a plurality of samples for flow cytometry analysis, the method comprising:
positioning a sample acquisition apparatus above a well plate comprising a plurality of wells; and
sequentially directing a flow of gas from the sample acquisition apparatus into each well in the plurality of wells, wherein:
the flow of gas from the sample acquisition apparatus into each well displaces a portion of a sample from each well in the plurality of wells into the sample acquisition apparatus; and
the sample acquisition apparatus does not move relative to the well plate, wherein:
each portion of the sample from each well in the plurality of wells directed into the sample acquisition apparatus is separated by a volume of gas from the flow of gas; and
the sample acquisition apparatus comprises:
a stack of plates;
a plurality of seals coupled to a first plate of the stack of plates, wherein each seal of the plurality of seals is configured to seal to a well in a well plate;
a first plurality of conduits extending through the stack of plates and the plurality of seals;
a plurality of gas valves, wherein each valve is in fluid communication with a conduit in the first plurality of conduits;
a sample port in a second plate of the stack of plates; and
a second plurality of conduits extending through the plurality of seals and the stack of plates, wherein the second plurality of conduits is in fluid communication with the sample port.

2. The method of claim 1 wherein the sample acquisition apparatus comprises:
a plurality of plates; and
a plurality of valves configured to allow the flow of gas to pass through the plurality of plates, wherein each valve in the plurality of valves is in fluid communication with a well in the plurality of wells.

3. The method of claim 2 wherein:
each valve of the plurality of valves is initially in the closed position; and
sequentially directing the flow of gas from the sample acquisition apparatus into each well in the plurality of wells comprises sequentially opening and closing the plurality of valves.

4. The method of claim 3 wherein:
the plurality of valves are arranged in a plurality of rows; and
sequentially opening and closing the plurality of valves comprises:
opening and closing a first valve in a first row in the plurality of valves;
opening and closing a second valve in the first row of the plurality of valves after the first valve has been opened and closed, wherein the second valve is adjacent to the first valve; and
opening and closing each valve in the first row, wherein each valve is opened and closed after an adjacent valve has been opened and closed.

5. The method of claim 4 wherein:
sequentially opening and closing the plurality of valves further comprises:
opening and closing a first valve in a second row in the plurality of valves;
opening and closing a second valve in the second row of the plurality of valves after the first valve has been opened and closed, wherein the second valve is adjacent to the first valve; and opening and closing each valve in the second row, wherein each valve is opened and closed after an adjacent valve has been opened and closed.

* * * * *